(12) United States Patent
Woehr

(10) Patent No.: US 7,160,269 B2
(45) Date of Patent: *Jan. 9, 2007

(54) SHORT CATHETER

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/327,206

(22) Filed: Jan. 6, 2006

(65) Prior Publication Data

US 2006/0184125 A1 Aug. 17, 2006

Related U.S. Application Data

(63) Continuation of application No. 10/779,370, filed on Feb. 13, 2004, which is a continuation of application No. 09/727,747, filed on Dec. 1, 2000, now Pat. No. 6,709,419.

(30) Foreign Application Priority Data

Dec. 1, 1999 (DE) .................. 229 21 084 U

(51) Int. Cl.
*A61M 5/178* (2006.01)

(52) U.S. Cl. .................. 604/164.07; 604/110; 604/198; 604/164.08

(58) Field of Classification Search .......... 604/110, 604/192, 164, 171, 198, 263, 243
See application file for complete search history.

(56) References Cited

U.S. PATENT DOCUMENTS

| 4,250,881 | A | 2/1981 | Smith |
| 4,790,828 | A | 12/1988 | Dombrowski et al. |
| 4,929,241 | A | 5/1990 | Kulli |
| 4,944,725 | A | 7/1990 | McDonald |
| 4,952,207 | A | 8/1990 | Lemieux |
| 4,978,344 | A | 12/1990 | Dombrowski et al. |
| 4,994,041 | A | 2/1991 | Dombrowski et al. |
| 5,049,136 | A | 9/1991 | Johnson |
| 5,053,017 | A | 10/1991 | Chamuel |
| 5,120,320 | A | 6/1992 | Fayngold |
| 5,135,504 | A | 8/1992 | McLees |
| 5,215,525 | A | 6/1993 | Sturman |

(Continued)

FOREIGN PATENT DOCUMENTS

EP 1 106 199 B1 6/2001

(Continued)

OTHER PUBLICATIONS

Woehr, K., U.S. Appl. No. 10/779,370, filed Feb. 13, 2004 entitled "Short Catheter", which is related to U.S. Appl. No. 11/327,206, filed Jan. 6, 2006 (13 pages).

(Continued)

*Primary Examiner*—Nicholas Lucchesi
*Assistant Examiner*—Theodore J. Stigell
(74) *Attorney, Agent, or Firm*—Christie, Parker & Hale, LLP

(57) ABSTRACT

A catheter assembly is provided which provides a flexible catheter tube having one end provided with a catheter hub. A hollow needle having a needle hub on its end is installed in the catheter tube with its sharp end extending out from one end of the catheter tube and a portion of the needle extending through the catheter hub. A needle shield, which is on the needle within the interior of the catheter hub, is biased axially within the catheter hub with its ends being fixed to prevent axial expansion.

25 Claims, 2 Drawing Sheets

U.S. PATENT DOCUMENTS

| | | | |
|---|---|---|---|
| 5,215,528 | A | 6/1993 | Purdy et al. |
| 5,217,438 | A | 6/1993 | Davis et al. |
| RE34,416 | E | 10/1993 | Lemieux |
| 5,279,570 | A | 1/1994 | Dombrowski et al. |
| 5,279,591 | A | 1/1994 | Simon |
| 5,300,045 | A | 4/1994 | Plassche, Jr. |
| 5,312,371 | A | 5/1994 | Dombrowski et al. |
| 5,322,517 | A | 6/1994 | Sircom et al. |
| 5,328,482 | A | 7/1994 | Sircom et al. |
| 5,344,408 | A | 9/1994 | Partika |
| 5,348,544 | A | 9/1994 | Sweeney et al. |
| 5,419,766 | A | 5/1995 | Chang et al. |
| 5,423,766 | A | 6/1995 | Di Cesare |
| 5,458,658 | A | 10/1995 | Sircom |
| 5,558,651 | A | 9/1996 | Crawford et al. |
| 5,599,310 | A | 2/1997 | Bogert |
| 5,611,781 | A | 3/1997 | Sircom et al. |
| 5,662,610 | A | 9/1997 | Sircom |
| 5,697,907 | A | 12/1997 | Gaba |
| 5,843,048 | A | 12/1998 | Gross |
| 5,882,337 | A | 3/1999 | Bogert et al. |
| 6,004,294 | A | 12/1999 | Brimhall et al. |
| 6,117,108 | A * | 9/2000 | Woehr et al. ............... 604/110 |
| 6,224,569 | B1 | 5/2001 | Brimhall |
| 6,280,419 | B1 * | 8/2001 | Vojtasek ..................... 604/192 |
| 6,287,278 | B1 | 9/2001 | Woehr et al. |
| 6,443,929 | B1 | 9/2002 | Kuracina et al. |
| 6,595,955 | B1 | 7/2003 | Ferguson et al. |
| 6,616,630 | B1 | 9/2003 | Woehr et al. |
| 6,749,588 | B1 | 6/2004 | Howell et al. |

FOREIGN PATENT DOCUMENTS

| | | |
|---|---|---|
| WO | WO 97/42989 | 11/1997 |
| WO | WO 99/08742 | 2/1999 |
| WO | WO 00/69501 | 11/2000 |

OTHER PUBLICATIONS

Office Action dated Jul. 28, 2005, U.S. Appl. No. 10/468,923, filed Feb. 2, 2004, Confirmation No. 2810, Examiner: Aamer S. Ahmed, (22 pages).

Notice of Opposition to European Patent Office dated Apr. 26, 2006 regarding Patent No. 1,106,199; Application No. 00 124 007.6, Opponents Ref. No. EPE-98 348 (19 pages) with Supporting Publications D1-D5: (D1) WO99/08742 (Publ. Date Feb. 25, 1999), (D2) WO 96/22800 (Publ. Date Aug. 1, 1996), (D3) EP 0 750 915 A2 (Publ. Date Jan. 2, 1997), (D4) US-B 5,662,610 (Publ. Date Sep. 2, 1997) and (D5) US-B 5,322,517 (Publ. Date Jun. 21, 1994).

* cited by examiner

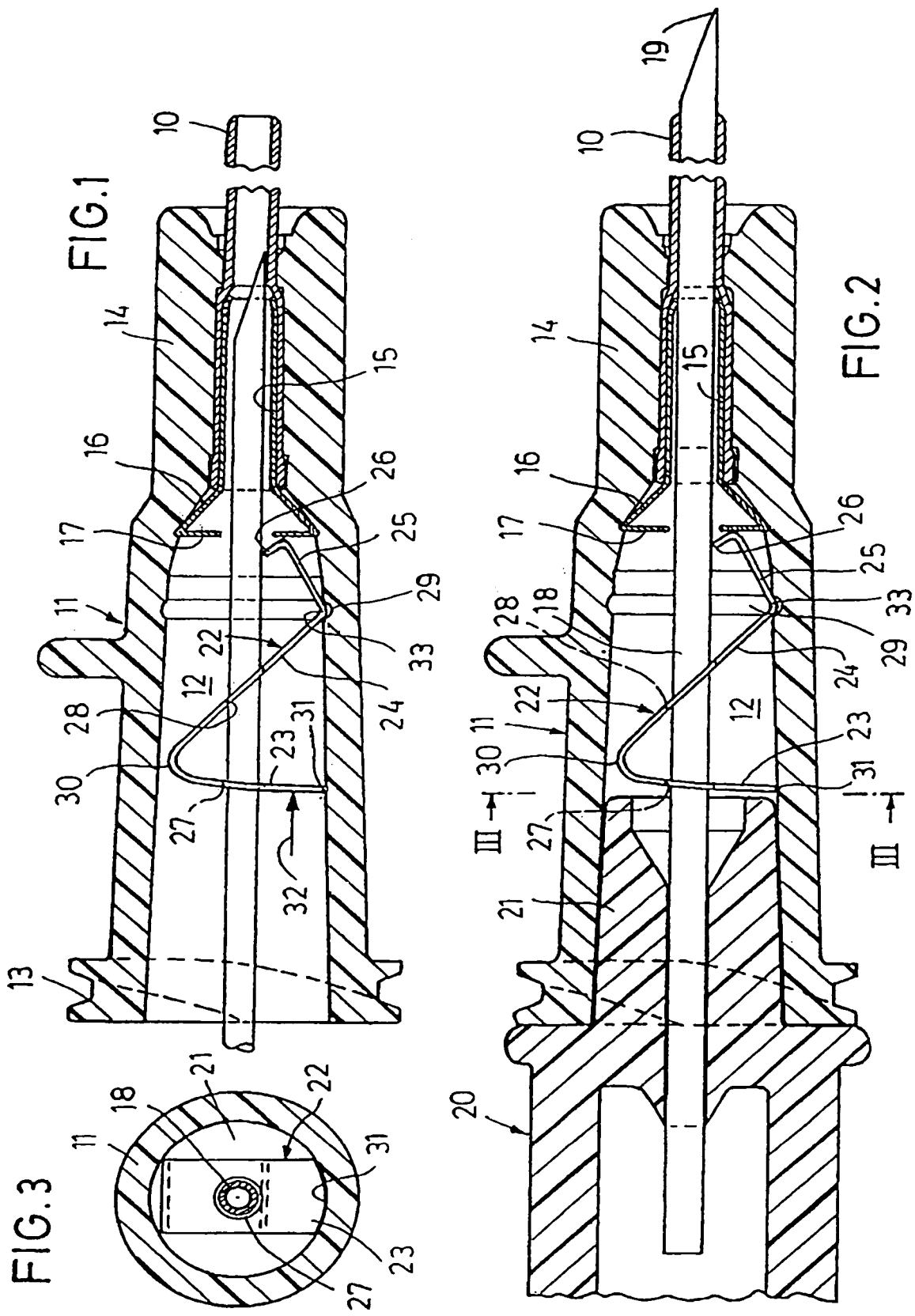

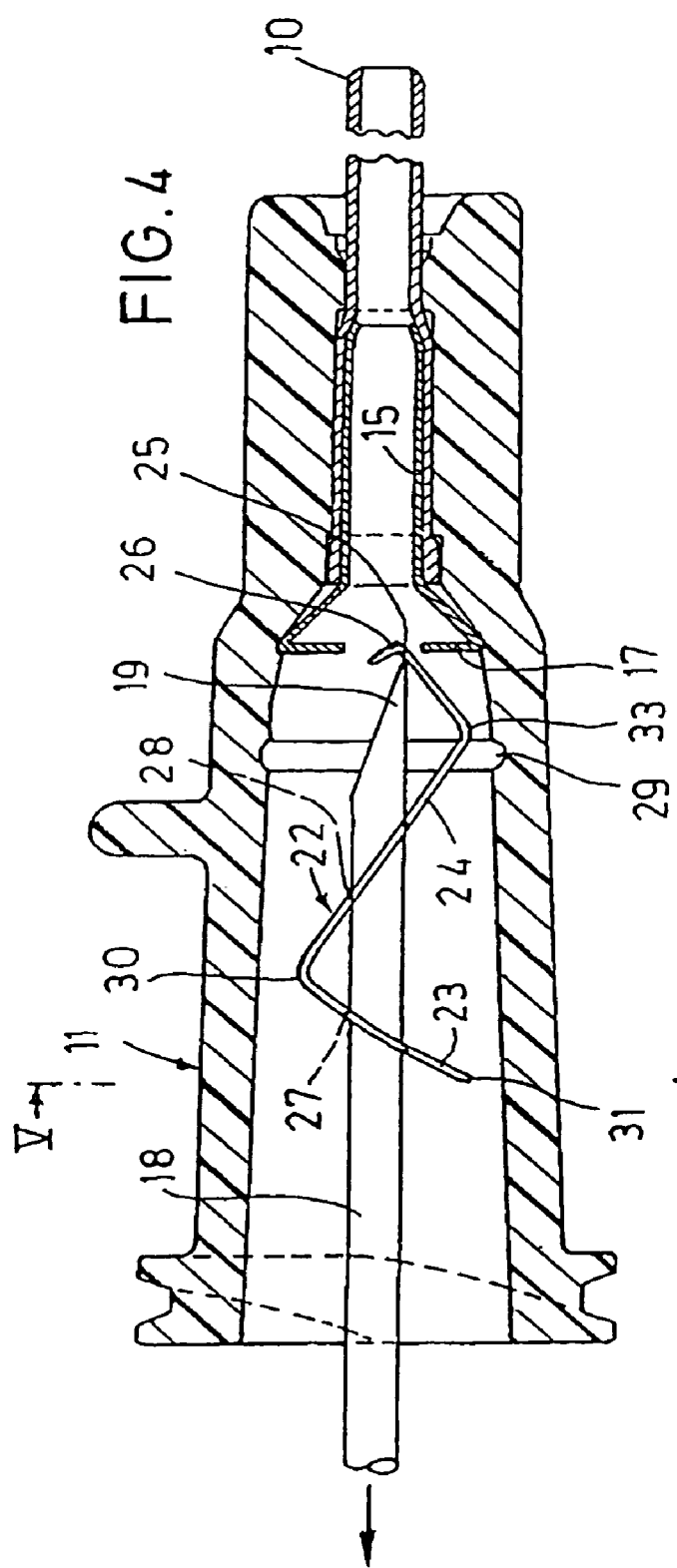
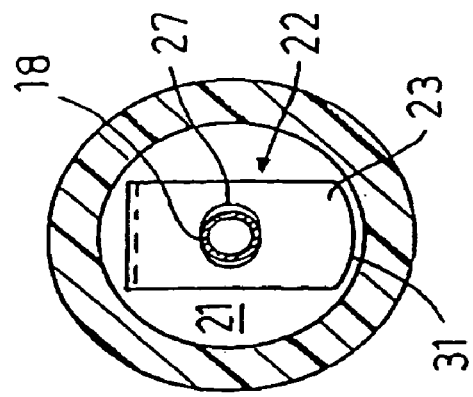

SHORT CATHETER

CROSS-REFERENCE TO RELATED APPLICATIONS

The present application is a continuation of Ser. No. 10/779,370, filed Feb. 13, 2004, which is a continuation application of Ser. No. 09/727,747, filed on Dec. 1, 2000, entitled "A SHORT CATHETER," now U.S. Pat. No. 6,709,419, which claims priority to German Utility Model DE 29921084.7, filed on Dec. 1, 1999, the contents of each of which are expressly incorporated herein by reference.

The present invention refers to a short catheter in which the needle inserted into the catheter tube is made unserviceable by a needle shield after withdrawal.

BACKGROUND

Short catheters are also referred to as vein catheters or IV-catheters. They have a flexible catheter tube having one end provided with a catheter hub. A hollow needle is inserted into the catheter tube, the needle having a cutting needle tip at the distal end and a needle hub at the proximal end. By the needle tip, the needle and the surrounding catheter tube is inserted into the body of a patient. When the needle tip has entered a vein, the needle is withdrawn.

From WO 99/08742, a short catheter is known, wherein the needle is provided with a needle shield. The needle shield consists of a elastic metal clamp that is contained in the cavity of the catheter hub and has holes for the passage of the needle. A hook member of the needle shield presses the needle from the side. When, upon the withdrawal of the needle, the needle tip passes the hook member, the hook member snaps over the needle tip so that the hook member covers the needle tip which is no longer accessible. Thus, people are kept safe from being injured by the needle tip. In particular, the danger of contamination by germs clinging to the needle, transferred when the needle was used for the first time, is reduced. The needle shield guarantees that the needle can be used only once so that a contaminated needle cannot be used with another patient. To prevent the needle shield from slipping beyond the distal needle end, the needle may be provided with a corresponding locking means in the form of a notch or a not circular portion forming a distal stop for limiting the movement of the needle shield.

It is an object of the present invention to provide a short catheter comprising a needle shield wherein a clamping effect firmly holds the needle shield in the needle tip covering position.

The present short catheter has the features mentioned in claim 1. According to the invention, the needle shield is biased axially within the needle shield, its ends being fixed to prevent axial expansion In the biased state, the needle may easily be pushed through the holes in the needle shield since the holes are orientated such that the needle is easily displaced. In the activated state, i.e., when the needle tip has passed the hook member, the hook member snaps over the needle tip, thus releasing the axial bias of the spring element. The spring element is thereby returned to its stretched original shape. Thus, the holes that previously surrounded the needle with a slight gap suddenly become narrower in one direction, whereby the spring element firmly engages the needle. The release of the axial tension and the return of the spring element cause a tight clamping of the needle at the edges of the holes in the spring element. Therefore, in many cases, locking or blocking means at the needle can be omitted so that the needle must not be modified with respect to conventional needles.

To be able to accommodate the axially compressed needle shield in the interior of the catheter hub, the catheter hub must be provided with a holding means forming a stop for the distal end of the needle shield, i.e. the hook member. Preferably, such a holding means is a metal member protruding into the catheter tube and supporting the same in the catheter hub. Such a metal member is usually provided in a catheter hub as an internal catheter support. The metal member may be modified in a simple manner to form an abutment shoulder for the needle shield. This abutment shoulder may be an end wall that is formed to the opening end of a funnel of the metal member.

Preferably, a proximal holding means consists of an end edge of the needle shield that projects into the wall of the catheter hub. This end edge may be sharpened and penetrate into the wall of the catheter hub, when the needle shield is mounted.

BRIEF DESCRIPTION OF THE DRAWINGS

The following is a detailed description of an embodiment of the invention with reference to the drawings, in which FIG. 1 is a longitudinal section through the short catheter, FIG. 2 is a longitudinal section after insertion of the needle into the short catheter being ready for use, FIG. 3 is a sectional view along line III—III in FIG. 2, FIG. 4 is a longitudinal section during withdrawal of the needle, and FIG. 5 is a sectional view along line V—V of FIG. 4.

DETAILED DESCRIPTION

The short catheter illustrated comprises a flexible catheter tube 10 of elastic plastic material having its proximal end provided with a catheter hub 11. The catheter hub 11 consists of an elongate hollow plastic member with a slightly conical interior 12 and a Luer connector 13 at the proximal end. The distal end portion 14 is tubular. The catheter tube 10 extends therethrough up to the interior 12. A tubular metal member 15 is inserted into the proximal end of the catheter tube 10, which expands the catheter tube and presses it against the wall of the tubular portion 14. At the proximal opening end of the metal member 15, the metal member is flared in the manner of a funnel 16. The opening end of the funnel 16 is formed with an end wall 17 directed radially inward.

A hollow needle 18 is inserted into the catheter tube 10, having a cutting needle tip 19 at the distal end. The needle 18 is made of steel. At the rear end, it is connected to a needle hub 20 of plastic material. The needle hub 20 abuts the proximal end of the catheter hub 11 and a frustoconical projection 21 thereof, loosely fitting into the catheter hub 11, protrudes into the interior 12.

The interior 12 accommodates the needle shield 22 consisting of a spring member made of bent spring steel sheet. The needle shield is generally bent in a Z-shape, with a rear leg 23, a middle leg 24 and a front leg 25 being provided in succession. The front leg 25 has a hook member 26 formed thereto, angled off by more than 90.degree.. The rear leg 23 and the middle leg 24 are each provided with a hole 27, 28.

As illustrated in FIG. 1, the needle shield 22 is inserted into the catheter hub 11 while sitting on the needle 18, the hook member 26 being set against the end wall 17 of the metal member 16. Then, using a tool (not illustrated) inserted into the interior 12 from the proximal end, an axial pressure is exerted in the direction of the arrow 32, the needle shield 22 being compressed in the axial direction. The axial direction follows the orientation of the axis of the catheter tube 10.

During the axial compression, a front bend 33 of the needle shield, formed between the sections 24 and 25, is pressed into an inner circumferential groove 29 of the interior. An opposite bend 30 connects the sections 23 and 24.

In this compressed state of the needle shield 22, the holes 27, 28 are circular in axial projection. This means that the hole 28 in the oblique middle leg 24 is oval and is larger in the longitudinal direction than in the transverse direction.

When the needle shield 22 is compressed axially, the end edge 31 of the section 23 is pressed into the wall of the catheter hub 11. Thus, the rear end of the needle shield penetrates into the wall, whereas the front end of the needle shield is supported on the end wall 17. In this state, the needle 18 may be inserted from the proximal end, passing through the holes 27 and 28 with a clearance and being advanced without any problems. The hook member 26 is displaced radially outward by the needle 18 so that, after further advancing the needle 18, it presses against the needle from the side.

FIGS. 4 and 5 illustrate the short catheter during the withdrawal of the needle 18 from the catheter tub 10 and the catheter hub 11. During the withdrawal of the needle 18, the hook member 26 that previously pressed against the needle from the side snaps over the needle tip 19. The previously axially compressed needle shield is relaxed and the end edge 31 comes clear of its engagement in the needle hub. The resilient needle shield 22 thus extends axially and the sharp edges of the holes 27, 28 firmly engage the needle 18. As can be seen in FIG. 5, the hole 27 becomes an ellipse, seen in axial projection. As soon as the needle shield has been activated by the needle tip 19 passing the hook member 26, the hook member 26 snaps over the needle tip and the needle shield firmly engages the needle. The hook member 26 now covers the needle tip and blocks any distal movement of the needle tip relative to the needle shield. The fact that the needle shield is axially expanded and separates from the catheter hub at its end edge 31 makes it freely movable within the catheter hub. After the needle shield is activated, its two holes 27, 28 engage a total of four points on the needle, as shown in FIG. 5. The needle 18 is a cylindrical round needle without any notches, projections or non-circular portions.

What is claimed is:

1. An IV catheter assembly comprising:
   (a) a first hub comprising an exterior surface, an interior surface defining an interior cavity, a proximal end, and a distal end;
   (b) a second hub comprising an exterior surface and an interior surface defining an interior cavity positioned substantially distally of the first hub and the distal end of the first hub contacts the interior cavity of the second hub when in a ready to use position;
   (c) a catheter tube defining a lumen connected to and extending distally away from the second hub;
   (d) a needle defining a needle shaft comprising a needle tip extending distally away from the distal end of the first hub and projecting through both the second hub and the catheter tube when in the ready to use position;
   (e) a tip protector positioned on the needle shaft comprising a proximal wall comprising a perimeter defining an opening surrounding the needle shaft, a movable leg extending distally of the proximal wall, and a tip blocking wall member extending at an end thereof;
   (f) wherein a wall surface on the proximal wall is orientated at a first angle to the shaft when the tip protector is in the ready to use position and is configured to self-orientate to a second angle to the shaft when the tip protector is in a protective position; and
   (g) wherein the opening of the proximal wall is configured to contact the needle shaft at two diametrically opposed locations along the perimeter of the opening and the tip blocking member is configured to move to a blocking position distal of the needle tip when the tip protector is in the protective position.

2. The IV catheter assembly of claim 1, wherein the first hub is a needle hub.

3. The IV catheter assembly of claim 1, wherein the tip protector is positioned, at least in part, inside the second hub.

4. The IV catheter assembly of claim 3, wherein the tip protector is an integrally formed unit.

5. The IV catheter assembly of claim 3, wherein the tip protector is made from a metallic material.

6. The IV catheter assembly of claim 3, wherein the second hub comprises a tapered cylinder comprising an open end.

7. The IV catheter of claim 6, wherein the second hub comprises a catheter hub.

8. The IV catheter assembly of claim 1, further comprising an opening on the movable leg.

9. The IV catheter assembly of claim 1, wherein the proximal wall contacts the interior cavity of the second hub.

10. The IV catheter assembly of claim 1, further comprising a finger member at an end of the tip blocking member.

11. The IV catheter assembly of claim 1, wherein the tip protector is configured to grip the needle in the absence of a needle crimp.

12. The IV catheter assembly of claim 1, wherein the second hub comprises a catheter hub.

13. The IV catheter assembly of claim 1, wherein the proximal wall comprises a non-contact end edge in the protective position.

14. An IV catheter assembly comprising:
   (a) a first hub comprising an exterior surface, an interior surface defining an interior cavity, a proximal end, and a distal end;
   (b) a second hub comprising an exterior surface and an interior surface defining an interior cavity positioned substantially distally of the first hub and the distal end of the first hub contacts the interior cavity of the second hub when in a ready to use position;
   (c) a catheter tube defining a lumen connected to and extending distally away from the second hub;
   (d) a needle defining a needle shaft comprising a needle tip extending distally away from the distal end of the first hub and projecting through both the second hub and the catheter tube when in the ready to use position;
   (e) a tip protector positioned on the needle shaft comprising a proximal wall comprising a perimeter defining an opening surrounding the needle shaft, and a movable leg comprising a tip blocking wall member extending at an end thereof;
   (f) the proximal wall on the tip protector being orientated generally vertically such that the opening is loose fitting around the needle shaft and the needle shaft is movable relative to the tip protector when moving from the ready to use position towards a protective position and being orientated less vertically when in the protective position such that the opening grips the needle shaft along at least two contact points spaced apart along the perimeter of the opening and the opening is no longer loose fitting due, at least in part, to the at least two contact points; and (g) wherein the tip protector is secured to the needle shaft and movement of the needle shaft relative to the tip protector is prohibited when in the protective position.

15. The IV catheter assembly of claim 14, wherein the first hub is a needle hub.

16. The IV catheter assembly of claim 14, wherein the second hub is a catheter hub.

17. The IV catheter assembly of claim 14, wherein the tip protector is positioned, at least in part, inside the interior cavity of the second hub.

18. The IV catheter assembly of claim 17, wherein the second hub comprises a tapered cylinder comprising an open end.

19. The IV catheter assembly of claim 18, wherein the second hub comprises a catheter hub.

20. The IV catheter assembly of claim 14, wherein the tip protector is an integrally formed unit.

21. The IV catheter assembly of claim 14, wherein the proximal wall contacts the interior cavity of the second hub.

22. A method for operating a catheter device assembly comprising:

(a) obtaining a first hub comprising an exterior surface, an interior surface defining an interior cavity, a proximal end, and a distal end;

(b) obtaining a second hub comprising an exterior surface and an interior surface defining an interior cavity positioned substantially distally of the first hub and the distal end of the first hub contacts the interior cavity of the second hub when in a ready to use position;

(c) extending a catheter tube defining a lumen distally away from the second hub and attaching the catheter tube to the second hub;

(d) extending a needle defining a needle shaft comprising a needle tip distally away from the distal end of the first hub and projecting the needle shaft through both the second hub and the catheter tube in the ready to use position;

(e) positioning a rip protector on the needle shaft, the tip protector comprising a proximal wall comprising a perimeter defining an opening surrounding the needle shaft and a movable leg comprising a tip blocking member extending at an end thereof;

(f) enclosing the tip protector inside a wall surface so that manipulation of the tip protector is prohibited when in the ready to use position;

(g) causing the proximal wall to cant over so that the opening on the proximal wall grips the needle shaft along at least two contact points diametrically opposed from one another to prohibit movement of the needle shaft relative to the tip protector; and (h) causing the tip blocking member to move to a blocking position in front of the needle tip.

23. The method of claim 22, wherein the first hub is a needle hub.

24. The method of claim 22, wherein the movable leg comprises an opening having the needle passing therethrough.

25. The method of claim 24, wherein the tip protector grips the needle with the opening on the movable leg in the blocking position.

* * * * *

UNITED STATES PATENT AND TRADEMARK OFFICE
CERTIFICATE OF CORRECTION

| | | |
|---|---|---|
| PATENT NO. | : 7,160,269 B2 | Page 1 of 1 |
| APPLICATION NO. | : 11/327206 | |
| DATED | : January 9, 2007 | |
| INVENTOR(S) | : Kevin Woehr | |

It is certified that error appears in the above-identified patent and that said Letters Patent is hereby corrected as shown below:

In column 6, line 9, in Claim 22, delete "rip" and insert -- tip --, therefor.

Signed and Sealed this

Ninth Day of November, 2010

David J. Kappos
*Director of the United States Patent and Trademark Office*